US012575798B2

(12) United States Patent  
Li

(10) Patent No.: US 12,575,798 B2  
(45) Date of Patent: Mar. 17, 2026

(54) SYSTEM AND METHOD FOR PET DATA COMPENSATION

(71) Applicant: SHANGHAI UNITED IMAGING HEALTHCARE CO., LTD., Shanghai (CN)

(72) Inventor: Jun Li, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 218 days.

(21) Appl. No.: 18/353,097

(22) Filed: Jul. 16, 2023

(65) Prior Publication Data

US 2023/0363725 A1 Nov. 16, 2023

Related U.S. Application Data

(63) Continuation of application No. PCT/CN2022/074821, filed on Jan. 28, 2022.

(30) Foreign Application Priority Data

Jan. 28, 2021 (CN) .......................... 202110116128.4

(51) Int. Cl.  
*A61B 6/03* (2006.01)  
*G06T 11/00* (2006.01)

(52) U.S. Cl.  
CPC ............ *A61B 6/037* (2013.01); *G06T 11/005* (2013.01)

(58) Field of Classification Search  
CPC ..... A61B 6/037; A61B 6/4266; A61B 6/4417; A61B 6/5205; A61B 6/52; G06T 11/003  
See application file for complete search history.

(56) References Cited

U.S. PATENT DOCUMENTS

| | | | |
|---|---|---|---|
| 5,249,123 A | 9/1993 | Hsieh | |
| 10,353,087 B1 * | 7/2019 | Aykac | ................... G01T 1/2985 |

(Continued)

FOREIGN PATENT DOCUMENTS

| | | |
|---|---|---|
| CN | 109124672 A | 1/2019 |
| CN | 109658473 A | 4/2019 |

(Continued)

OTHER PUBLICATIONS

Jones et al., "Tracking Coincidence Events in PET Even When Count Rates Are Extremely High: The Lost-Event Tally Packet Concept," IEEE Transactions on Nuclear Science, vol. 59, No. 5, Oct. 2012. (Year: 2012).*  
Lu, Yao et al., Spectrum-analyzing Laser Doppler Anemometry Signal Processor Based on DSP, Opto-Electronic Engineering, 34(1): 126-130, 2007.  
International Search Report in PCT/CN2022/074821 mailed on May 6, 2022, 5 pages.

(Continued)

*Primary Examiner* — Casey Bryant  
(74) *Attorney, Agent, or Firm* — METIS IP LLC

(57) ABSTRACT

The present disclosure provides a PET data compensation system and method. The method may include obtaining a count of missing data of first coincidence data. The method may also include obtaining second coincidence data and a second count of the second coincidence data, the second coincidence data and the missing data constituting the first coincidence data. The method may further include performing a compensation relating to the second coincidence data based on at least two of the count of the missing data, a first count of the first coincidence data, or the second count of the second coincidence data.

19 Claims, 9 Drawing Sheets

1100

Detecting a full signal of at least a part of the one or more buffer memories in the coincidence detection apparatus — 1110

Monitoring writing signals received by the at least a part of the one or more buffer memories — 1120

Determining a first missing count of a first portion of the missing data according to a count of the writing signals — 1130

Obtaining a third count of third coincidence data output by the coincidence detection apparatus and a second count of second coincidence data input into the processing device — 1140

Determining a difference between the third count of third coincidence data output by the coincidence detection apparatus and the second count of second coincidence data input into the processing device as a second missing count of a second portion of the missing data — 1150

Determining the count of the missing data by summing up the first missing count and the second missing count — 1160

(56)                    References Cited

U.S. PATENT DOCUMENTS

| 2009/0090868 | A1 | 4/2009 | Payne |
| 2016/0073993 | A1 | 3/2016 | Ouyang et al. |
| 2017/0371046 | A1 | 12/2017 | Laurence et al. |
| 2018/0203141 | A1 | 7/2018 | Chang et al. |
| 2019/0049605 | A1 | 2/2019 | Dong |

FOREIGN PATENT DOCUMENTS

| CN | 111084633 | A | 5/2020 |
| CN | 111728633 | A | 10/2020 |
| EP | 1113293 | A2 | 7/2001 |
| WO | 2016110804 | A1 | 7/2016 |
| WO | 2022161478 | A1 | 8/2022 |

OTHER PUBLICATIONS

Written Opinion in PCT/CN2022/074821 mailed on May 6, 2022, 5 pages.
First Office Action in Chinese Application No. 202110116128.4 mailed on Apr. 22, 2022, 17 pages.
W. F. Jones et al., Tracking Coincidence Events in PET Even When Count Rates Are Extremely High: The Lost-Event Tally Packet Concept, IEEE Transactions on Nuclear Science, 59(5): 1915-1919, 2012.
Paul E. Kinahan et al., Positron Emission Tomography-Computed Tomography Standardized Uptake Values in Clinical Practice and Assessing Response to Therapy, Seminars in Ultrasound, CT and MRI, 31(6): 496-505, 2010.
The Extended European Search Report in European Application No. 22745350.3 mailed on Apr. 12, 2024, 11 pages.

* cited by examiner

300

500

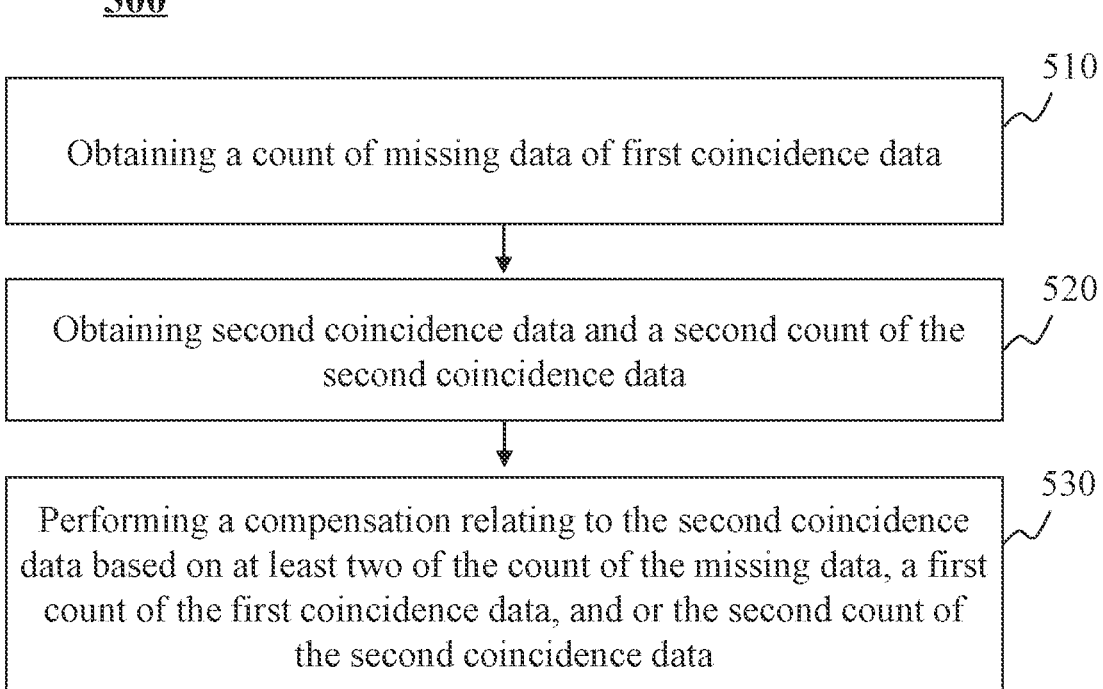

510

Obtaining a count of missing data of first coincidence data

520

Obtaining second coincidence data and a second count of the second coincidence data

530

Performing a compensation relating to the second coincidence data based on at least two of the count of the missing data, a first count of the first coincidence data, and or the second count of the second coincidence data

FIG. 5

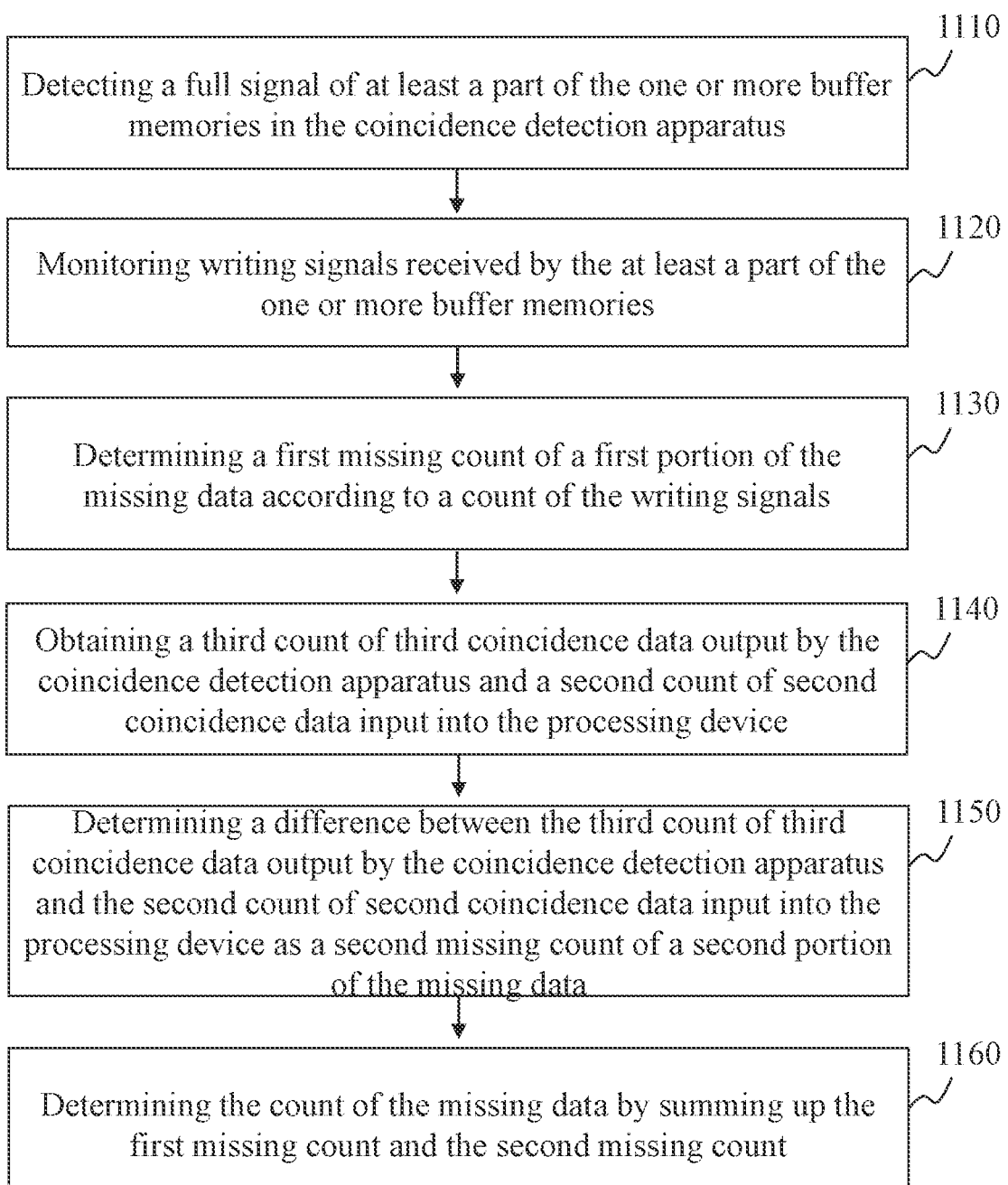

1100

1110

Detecting a full signal of at least a part of the one or more buffer memories in the coincidence detection apparatus

1120

Monitoring writing signals received by the at least a part of the one or more buffer memories

1130

Determining a first missing count of a first portion of the missing data according to a count of the writing signals

1140

Obtaining a third count of third coincidence data output by the coincidence detection apparatus and a second count of second coincidence data input into the processing device

1150

Determining a difference between the third count of third coincidence data output by the coincidence detection apparatus and the second count of second coincidence data input into the processing device as a second missing count of a second portion of the missing data

1160

Determining the count of the missing data by summing up the first missing count and the second missing count

FIG. 11

SYSTEM AND METHOD FOR PET DATA COMPENSATION

CROSS-REFERENCE TO RELATED APPLICATIONS

This application is a continuation of International Application No. PCT/CN2022/074821, filed on Jan. 28, 2022, which claims priority to Chinese Patent Application No. 202110116128.4, filed on Jan. 28, 2021, the contents of each of which are hereby incorporated by reference.

TECHNICAL FIELD

The present disclosure generally relates to systems and methods for data correction, and more particularly, to systems and methods for compensating coincidence data.

BACKGROUND

A Positron Emission Computed tomography (PET) technology has been widely used in clinical examination and disease diagnosis. In some cases, when a subject (e.g., a patient) or a portion thereof needs a medical diagnosis and/or treatment, the subject may be scanned, and coincidence data of the subject may be generated. However, data loss of the coincidence data usually occurs in the buffering and/or the transmission of the coincidence data if a high-activity radionuclide is used during the scan. The data loss may result in an inaccurate processing result (e.g., a PET image, a Standard Uptake Value (SUV), etc.). Thus, it is desirable to provide systems and methods for data compensation to reduce, remove or eliminate the effect of the data loss effectively and efficiently.

SUMMARY

According to one aspect of the present disclosure, a system is provided. The system may include at least one storage medium including a set of instructions; and at least one processor configured to communicate with the at least one storage medium, wherein when executing the set of instructions. The at least one processor is configured to direct the system to perform operations including obtaining a count of missing data of first coincidence data; obtaining second coincidence data and a second count of the second coincidence data, the second coincidence data and the missing data constituting the first coincidence data; performing a compensation relating to the second coincidence data based on at least two of the count of the missing data, a first count of the first coincidence data, or the second count of the second coincidence data.

According to another aspect of the present disclosure, a method implemented on a computing device having a processor and a computer-readable storage device is provided. The method may include obtaining a count of missing data of first coincidence data; obtaining second coincidence data and a second count of the second coincidence data, the second coincidence data and the missing data constituting the first coincidence data; performing a compensation relating to the second coincidence data based on at least two of the count of the missing data, a first count of the first coincidence data, or the second count of the second coincidence data.

According to a further aspect of the present disclosure, a non-transitory readable medium including at least one set of instructions is provided. When executed by at least one processor of a computing device, the at least one set of instructions may direct the at least one processor to perform a method. The method may include obtaining a count of missing data of first coincidence data; obtaining second coincidence data and a second count of the second coincidence data, the second coincidence data and the missing data constituting the first coincidence data; performing a compensation relating to the second coincidence data based on at least two of the count of the missing data, a first count of the first coincidence data, or the second count of the second coincidence data.

In some embodiments, the count of the missing data includes at least one of a first missing count or a second missing count, the first missing count being resulted from buffering of the first coincidence data, and the second missing count being resulted from transmission of a portion of the first coincidence data.

In some embodiments, the first missing count equals a total count of first writing signals being received by at least a part of one or more buffer memories, each of the first writing signals being received when a full signal is received from one of the at least a part of one or more buffer memories, the one or more buffer memories being configured for the buffering of the first coincidence data.

In some embodiments, the first missing count is detected by a first counting device, the first counting device being configured to monitor the first writing signals.

In some embodiments, the second missing count equals a difference between a third count of third coincidence data outputted by a coincidence detection apparatus and the second count of the second coincidence data, the data transmission device being configured for the transmission of the first coincidence data.

In some embodiments, the second missing count is detected by a second counting device, the second counting device being configured to monitor an output of the coincidence detection apparatus.

In some embodiments, the performing a compensation relating to the second coincidence data based on at least two of the count of the missing data, a first count of the first coincidence data, or the second count of the second coincidence data includes: determining a preliminary Standard Uptake Value (SUV) based on the second coincidence data; determining a compensation coefficient based on the at least two of the count of the missing data, the first count of the first coincidence data, or the second count of the second coincidence data; and generating a compensated SUV by compensating the preliminary SUV using the compensation coefficient.

In some embodiments, the determining a compensation coefficient based on the at least two of the count of the missing data, the first count of the first coincidence data, or the second count of the second coincidence data includes: determining a ratio relating to the at least two of the count of the missing data, the first count of the first coincidence data, or the second count of the second coincidence data; and designating the ratio as the compensation coefficient.

In some embodiments, the determining a compensation coefficient based on the at least two of the count of the missing data, the first count of the first coincidence data, or the second count of the second coincidence data includes: obtaining a compensation coefficient determination model; and determining the compensation coefficient based on the compensation coefficient determination model and the at least two of the count of the missing data, the first count of the first coincidence data, or the second count of the second coincidence data.

In some embodiments, the generating a compensated SUV by compensating the preliminary SUV using the compensation coefficient includes: generating the compensated SUV by multiplying the preliminary SUV by the compensation coefficient.

In some embodiments, the performing a compensation relating to the second coincidence data based on at least two of the count of the missing data, a first count of the first coincidence data, or the second count of the second coincidence data includes: determining a compensation coefficient based on the at least two of the count of the missing data, a first count of the first coincidence data, or the second count of the second coincidence data; and compensating the second count of the second coincidence data using the compensation coefficient.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 5 includes a flowchart illustrating an exemplary process for compensating PET data according to some embodiments of the present disclosure;

FIG. 11 includes a flowchart illustrating an exemplary process for obtaining a count of missing data in a transmission path of the first coincidence data according to some embodiments of the present disclosure.

DETAILED DESCRIPTION

Figure 1:
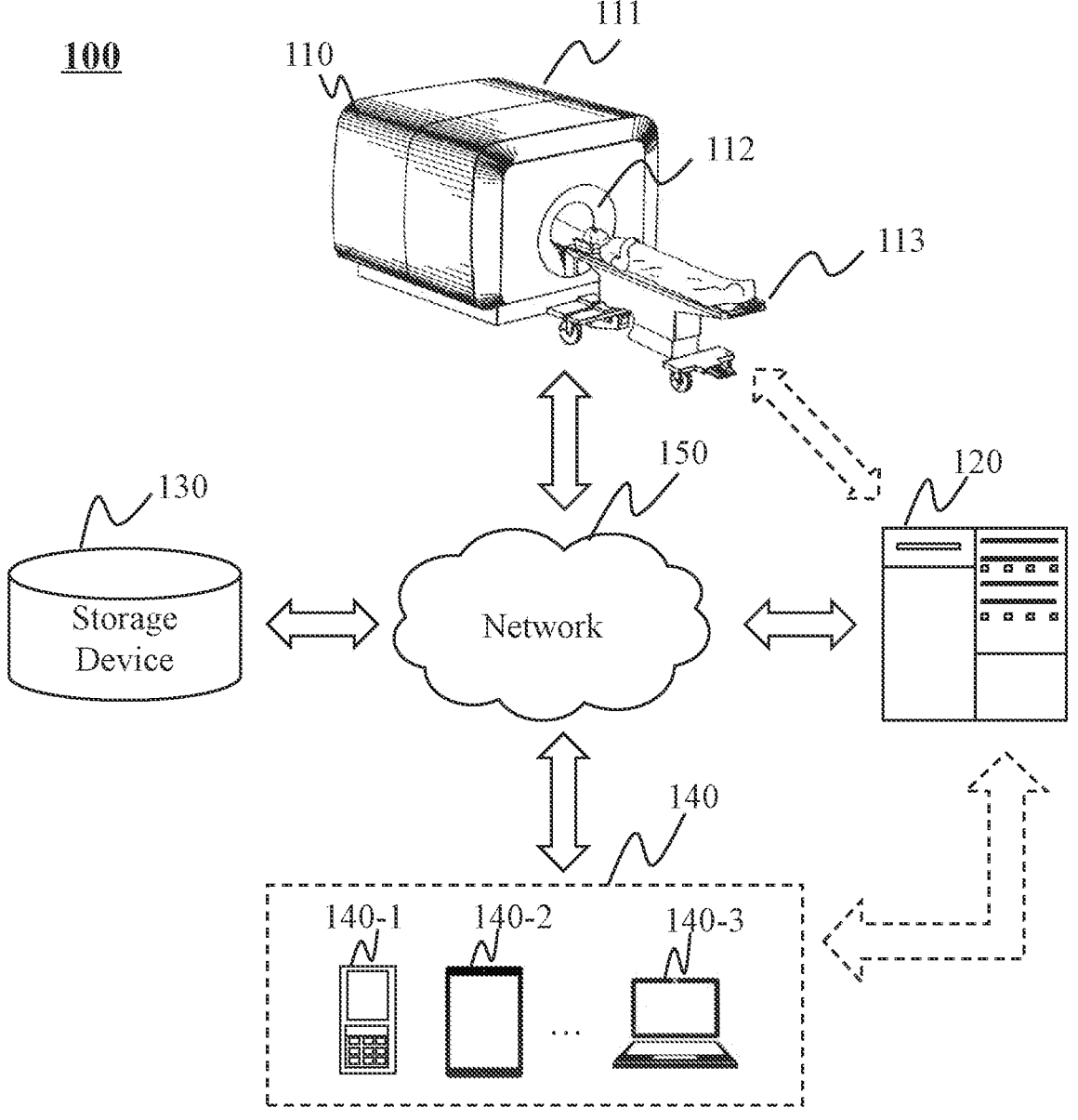
FIG. 1 is a schematic diagram illustrating an exemplary data compensation system 100 according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by another expression if they may achieve the same purpose.

It will be understood that when a unit, engine, module or block is referred to as being "on," "connected to," or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The flowcharts used in the present disclosure illustrate operations that systems implement according to some embodiments of the present disclosure. It is to be expressly understood the operations of the flowcharts may be implemented not in order. Conversely, the operations may be implemented in an inverted order, or simultaneously. Moreover, one or more other operations may be added to the flowcharts. One or more operations may be removed from the flowcharts.

Provided herein are systems and methods for non-invasive imaging, such as for disease diagnosis, treatment, and/or research purposes. In some embodiments, the imaging system may include a single modality system and/or a multi-modality system. The term "modality" used herein broadly refers to an imaging or treatment method or technology that gathers, generates, processes, and/or analyzes imaging information of a subject or treatments the subject. The single modality system may include a Positron Emission Tomography (PET) system. The multi-modality system may include a Positron Emission Tomography-Computed Tomography (PET-CT) system, a Positron Emission Tomography-Magnetic Resonance Imaging (PET-MR) system, a Positron Emission Tomography-X-ray Imaging (PET-X-ray) system, or the like, or any combination thereof.

According to an aspect of the present disclosure, systems and methods for PET data compensation are provided. A count of missing data of first coincidence data and second coincidence data may be obtained. The second coincidence data and the missing data may constitute the first coincidence data. A compensation relating to the second coincidence data may be performed on, e.g., parameter values of one or more parameters relating to a subject, the second coincidence data, a PET image of the subject, etc., based on at least two of the count of the missing data, a first count of the first coincidence data, or the second count of the second coincidence data. For instance, a preliminary Standard Uptake Value (SUV) may be determined based on the second coincidence data. A compensation coefficient may be determined based on at least two of the count of the missing data, a first count of the first coincidence data, or the second count of the second coincidence data. The preliminary SUV may be compensated using the compensation coefficient. In this way, the compensated SUV may be more accurate and closer to an actual SUV.

FIG. 1 is a schematic diagram illustrating an exemplary data compensation system 100 according to some embodiments of the present disclosure. As illustrated, the data compensation system 100 may include a scanner 110, a processing device 120, a storage device 130, one or more terminals 140, and a network 150. The components in the data compensation system 100 may be connected in various ways. Merely by way of example, as illustrated in FIG. 1, the scanner 110 may be connected to the processing device 120 through the network 150. As another example, the scanner 110 may be connected with the processing device 120 directly as indicated by the bi-directional arrow in dotted lines linking the scanner 110 and the processing device 120. As a further example, the storage device 130 may be connected with the processing device 120 directly (not shown in FIG. 1) or through the network 150. As still a further example, one or more terminal(s) 140 may be connected with the processing device 120 directly (as indicated by the bi-directional arrow in dotted lines linking the terminal(s) 140 and the processing device 120) or through the network 150.

The scanner 110 may scan a subject or a portion thereof that is located within its detection region, and generate scanning data relating to the (portion of) subject. The scanner 110 may include a PET scanner. In some embodiment, the scanner 110 may be a multi-modality device including two or more scanners exemplified above. For example, the scanner 110 may be a PET-CT scanner, a PET-MR scanner, etc. The following descriptions are provided, unless otherwise stated expressly, with reference to a PET scanner for illustration purposes and not intended to be limiting.

The PET scanner may include a gantry 111, a detecting region 112, and a scanning bed 113. The gantry 111 may support a plurality of detectors and an electronic assembly (not shown). A subject may be placed on the scanning bed 113 for a PET scan.

To prepare for a PET scan, a radionuclide (also referred to as "PET tracer" or "PET tracer molecules") may be introduced into the subject. The PET tracer may emit positrons in the detecting region 112 when it decays. An annihilation (also referred to as "annihilation event" or "annihilation reaction") may occur when a positron collides with an electron. The annihilation may produce two photons (e.g., gamma photons), which may travel in opposite directions. A line connecting detectors that detecting the two gamma photons may be defined as a "Line of Response (LOR). The plurality of detectors set on the gantry 111 may detect, gamma photons emitted from the detecting region 112 and generate electrical signals representing information (e.g., time information, energy information) of detected photons. The electronic assembly may include a coincidence detection apparatus configured to detect coincidence events based on the electrical signals. The coincidence events (also referred to as coincidence data) may be used to generate PET data (also referred to as scanning data). In some embodiments, the one or more detectors used in the PET scan may include crystal elements and Photomultiplier Tubes (PMT).

The processing device 120 may process data and/or information obtained and/or retrieve from the scanner 110, the terminal(s) 140, the storage device 130 and/or other storage devices. In some embodiments, the processing device 120 may be a single server or a server group. The server group may be centralized or distributed. In some embodiments, the processing device 120 may be local or remote. For example, the processing device 120 may access information and/or data stored in the scanner 110, the terminal(s) 140, and/or the storage device 130 via the network 150. As another example, the processing device 120 may be directly connected with the scanner 110, the terminal(s) 140, and/or the storage device 130 to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 120 may be implemented on a computing device 200 having one or more components illustrated in FIG. 2 in the present disclosure.

The storage device 130 may store data and/or instructions. In some embodiments, the storage device 130 may store data obtained from the scanner 110, the terminal(s) 140, and/or the processing device 120. In some embodiments, the storage device 130 may store data and/or instructions that the processing device 120 may execute or use to perform exemplary methods described in the present disclosure. In some embodiments, the storage device 130 may include a mass storage device, a removable storage device, a volatile read-and-write memory, a read-only memory (ROM), or the like, or any combination thereof. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected with the network 150 to communicate with one or more components of the data compensation system 100 (e.g., the processing device 120, the terminal(s) 140, etc.). One or more components of the data compensation system 100 may access the data or instructions stored in the storage device 130 via the network 150. In some embodiments, the storage device 130 may be directly connected or communicate with one or more components of the data compensation system 100 (e.g., the processing device 120, the terminal(s) 140, etc.). In some embodiments, the storage device 130 may be part of the processing device 120.

The terminal(s) 140 may include a mobile device 140-1, a tablet computer 140-2, a laptop computer 140-3, or the like, or any combination thereof. In some embodiments, the mobile device 140-1 may include a smart home device, a wearable device, a smart mobile device, a virtual reality device, an augmented reality device, or the like, or any combination thereof. In some embodiments, the smart home device may include a control device of an intelligent electronic apparatus, a smart monitoring device, a smart television, a smart video camera, an interphone, or the like, or any combination thereof. In some embodiments, the terminal(s) 140 may remotely operate the scanner 110. In some embodiments, the terminal(s) 140 may operate the scanner 110 via a wireless connection. In some embodiments, the terminal(s) 140 may receive information and/or instructions inputted by a user, and send the received information and/or instructions to the scanner 110 or the processing device 120 via the network 150. In some embodiments, the terminal(s) 140 may receive data and/or information from the processing device 120. In some embodiments, the terminal(s) 140 may be part of the processing device 120. In some embodiments, the terminal(s) 140 may be omitted.

The network 150 may include any suitable network that can facilitate the exchange of information and/or data for the data compensation system 100. In some embodiments, one or more components of the data compensation system 100 (e.g., the scanner 110, the terminal(s) 140, the processing device 120, or the storage device 130) may communicate information and/or data with one or more other components of the data compensation system 100 via the network 150. In some embodiments, the network 150 may be any type of wired or wireless network, or a combination thereof. In some embodiments, the network 150 may include one or more network access points. For example, the network 150 may include wired and/or wireless network access points such as base stations and/or internet exchange points through which one or more components of the data compensation system 100 may be connected with the network 150 to exchange data and/or information.

It should be noted that the above description of the data compensation system 100 is merely provided for the purposes of illustration, not intended to limit the scope of the present disclosure. For persons having ordinary skills in the art, components contained in the data compensation system 100 may be combined or adjusted in various ways, or connected with other components as sub-systems, and various variations and modifications may be conducted under the teaching of the present disclosure. However, those variations and modifications may not depart the spirit and scope of this disclosure. For example, the scanner 110 may be a standalone device external to the data compensation system 100, and the data compensation system 100 may be connected to or in communication with the scanner 110 via the network 150. All such modifications are within the protection scope of the present disclosure.

Figure 2:
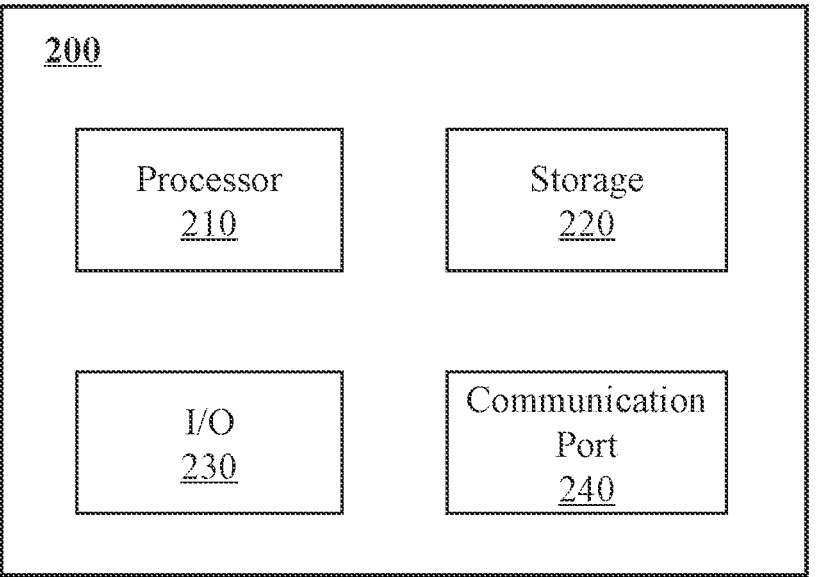
FIG. 2 is a schematic diagram illustrating hardware and/or software components of an exemplary computing device according to some embodiments of the present disclosure.

FIG. 2 is a schematic diagram illustrating hardware and/or software components of an exemplary computing device 200 on which the processing device 120 may be implemented according to some embodiments of the present disclosure. As illustrated in FIG. 2, the computing device 200 may include a processor 210, storage 220, an input/output (I/O) 230, and a communication port 240.

The processor 210 may execute computer instructions (program code) and perform functions of the processing device 120 in accordance with techniques described herein. The computer instructions may include, for example, routines, programs, objects, components, signals, data structures, procedures, modules, and functions, which perform particular functions described herein. For example, the processor 210 may process data obtained from the scanner 110, the terminal(s) 140, the storage device 130, and/or any other component of the data compensation system 100. In some embodiments, the processor 210 may perform instructions obtained from the terminal(s) 140. In some embodiments, the processor 210 may include one or more hardware processors, such as a microcontroller, a microprocessor, a Reduced Instruction Set Computer (RISC), an Application Specific Integrated Circuits (ASICs), an Application-Specific Instruction-Set Processor (ASIP), a Central Processing Unit (CPU), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the scanner 110, the terminal(s) 140, the storage device 130, or any other component of the data compensation system 100. In some embodiments, the storage 220 may include a mass storage device, a removable storage device, a volatile read-and-write memory, a Read-Only Memory (ROM), or the like, or any combination thereof. In some embodiments, the storage 220 may store one or more programs and/or instructions to perform exemplary methods described in the present disclosure. For example, the storage 220 may store a program for the processing device 120 for reducing noise in an image.

The I/O 230 may input or output signals, data, and/or information. In some embodiments, the I/O 230 may enable user interaction with the processing device 120. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a Liquid Crystal Display (LCD), a Light-Emitting Diode (LED)-based display, a flat panel display, a curved screen, a television device, a Cathode Ray Tube (CRT), or the like, or a combination thereof.

The communication port 240 may be connected with a network (e.g., the network 150) to facilitate data communications. The communication port 240 may establish connections between the processing device 120 and the scanner 110, the terminal(s) 140, or the storage device 130. The connection may be a wired connection, a wireless connection, or a combination of both that enables data transmission and reception. In some embodiments, the communication port 240 may be a specially designed communication port. For example, the communication port 240 may be designed in accordance with the digital imaging and communications in medicine (DICOM) protocol.

Figure 3:
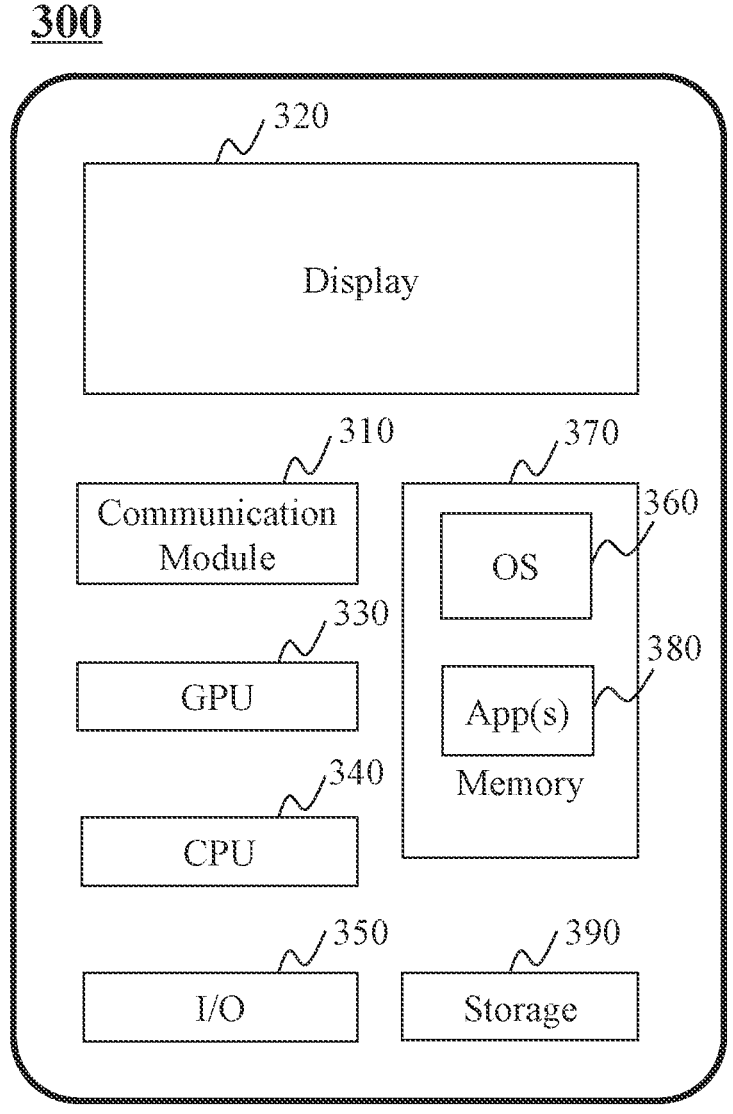
FIG. 3 is a schematic diagram illustrating hardware and/or software components of an exemplary mobile device according to some embodiments of the present disclosure.

FIG. 3 is a schematic diagram illustrating hardware and/or software components of an exemplary mobile device 300 according to some embodiments of the present disclosure. As illustrated in FIG. 3, the mobile device 300 may include a communication module 310, a display 320, a graphics processing unit (GPU) 330, a central processing unit (CPU) 340, an I/O 350, a memory 370, and storage 390. In some embodiments, any other suitable component, including but not limited to a system bus or a controller (not shown), may also be included in the mobile device 300. In some embodiments, a mobile operating system 360 (e.g., iOS, Android, Windows Phone, etc.) and one or more applications 380 may be loaded into the memory 370 from the storage 390 in order to be executed by the CPU 340. The applications 380 may include a browser or any other suitable mobile apps for receiving and rendering information relating to data processing or other information from the processing device 120. User interactions with the information stream may be achieved via the I/O 350 and provided to the processing device 120 and/or other components of the data compensation system 100 via the network 150.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate an imaging report as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4:
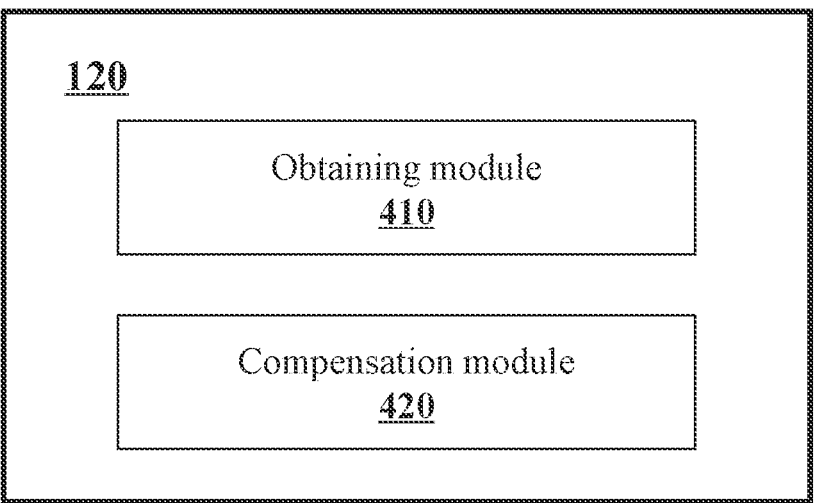
FIG. 4 is a block diagram illustrating an exemplary processing device according to some embodiments of the present disclosure.

FIG. 4 is a block diagram illustrating an exemplary processing device according to some embodiments of the present disclosure. The processing device 120 may include an obtaining module 410, and a compensation module 420. One or more of the modules of the processing device 120 may be interconnected. The connection(s) may be wireless or wired. At least a portion of the processing device 120 may be implemented on a computing apparatus as illustrated in FIG. 2 or a mobile device as illustrated in FIG. 3.

The obtaining module 410 may obtain data and/or information. The obtaining module 410 may obtain data and/or information from the scanner 110, the storage device 130, the terminal(s) 140, or any devices or components capable of storing data via the network 150. In some embodiments, the obtaining module 410 may obtain a count of missing data of first coincidence data. Details regarding the obtaining of the count of the missing data may be found elsewhere in the present disclosure. See, for example, FIGS. 7-11 and the descriptions thereof. In some embodiments, the obtaining module 410 may also obtain second coincidence data. The second coincidence data may be coincidence data received by the processing device (e..g, the processing device 120) or a storage device from the data transmission device. The second coincidence data and the missing data may constitute the first coincidence data.

The compensation module 420 may perform a compensation based on the count of the missing data and the second coincidence data. In some embodiments, the compensation module 420 may perform the compensation on one or more parameters relating to the subject, the second coincidence data, a PET image of the subject, etc. The one or more parameters may include, for example, a standard uptake value (SUV), a radioactivity concentration, etc.

It should be noted that the above descriptions of the processing device 120 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the processing device 120 may include one or more other modules. In some embodiments, two or more units in the processing device 120 may form one module. However, those variations and modifications also fall within the scope of the present disclosure.

FIG. 5 includes a flowchart illustrating an exemplary process for compensating PET data according to some embodiments of the present disclosure. In some embodiments, at least a portion of the process 500 may be performed by the processing device 120 (e.g., implemented in the computing device 200 shown in FIG. 2, the processing device illustrated in FIG. 4). In some embodiments, at least a portion of the process 500 may be performed by a terminal device (e.g., the mobile device 300 shown in FIG. 3) embodying software and/or hardware.

In 510, the processing device 120 (e.g., the obtaining module 410 or the processor 210) may obtain a count of missing data of first coincidence data.

The first coincidence data refers to coincidence events (e..g, true coincidence events, random coincidence events, scatter coincidence events) that are generated in theory based on detected signals (e.g., electrical signals) of detectors of the scanner 110. For instance, after a radionuclide is introduced into the subject, annihilation reactions each of which produces two photons (i.e., a pair of photons) (e.g., gamma photons) may occur. Detectors set on the gantry 111 of the scanner 110 may detect multiple pairs of photons (e.g., gamma photons) emitted from the subject and generate the detected signals. The detected signals may be processed by a coincidence detection apparatus of the PET scanner. The coincidence detection apparatus may include a coincidence detection module and a data cache module. The coincidence detection module may be configured to process the detected signal and generate the first coincidence data. A generation speed of the first coincidence data may be greater than a recording speed of the first coincidence data. The generation speed refers to a speed or rate at which the first coincidence data is generated by the coincidence detection module. The recording speed refers to a speed or rate at which the first coincidence data is recorded by the coincidence detection apparatus. In this case, the data cache module may be provided to store at least a portion of the first coincidence data and output the at least a portion of the first coincidence events (also referred to as third coincidence events) to a data transmission device. The data transmission device may transmit at least a portion of the third coincidence events to a processing device (e.g., the processing device 120) via a data transmission link (i.e., a data transmission path). For example, the at least a portion of the third coincidence data may be transmitted, by the data transmission device, to the processing device 120 for further processing (e.g., determining a standard uptake value (SUV), generating a PET image of the subject, etc.) In some embodiments, in the buffering process of the first coincidence events, data loss may occur such that a first portion of the first coincidence data may be lost as the buffering and a second portion (i.e., the remaining portion) of the first coincidence data (also referred to as third coincidence data) may be outputted by the coincidence detection apparatus. In some embodiments, in the buffering process of the first coincidence data, data loss may not occur such that all of the first coincidence data may be outputted by the coincidence detection apparatus, in other words, the first coincidence data may be the same as the third coincidence data. In some embodiments, in the transmission process of the third coincidence data, data loss may occur (e.g., in the transmission of the third coincidence data) such that at least a portion of the third coincidence data (i.e., second coincidence data) may be received by the processing device or the storage device for further processing. Data lost in the buffering and transmission process may also be referred to as the missing data of the first coincidence data.

Figure 6:
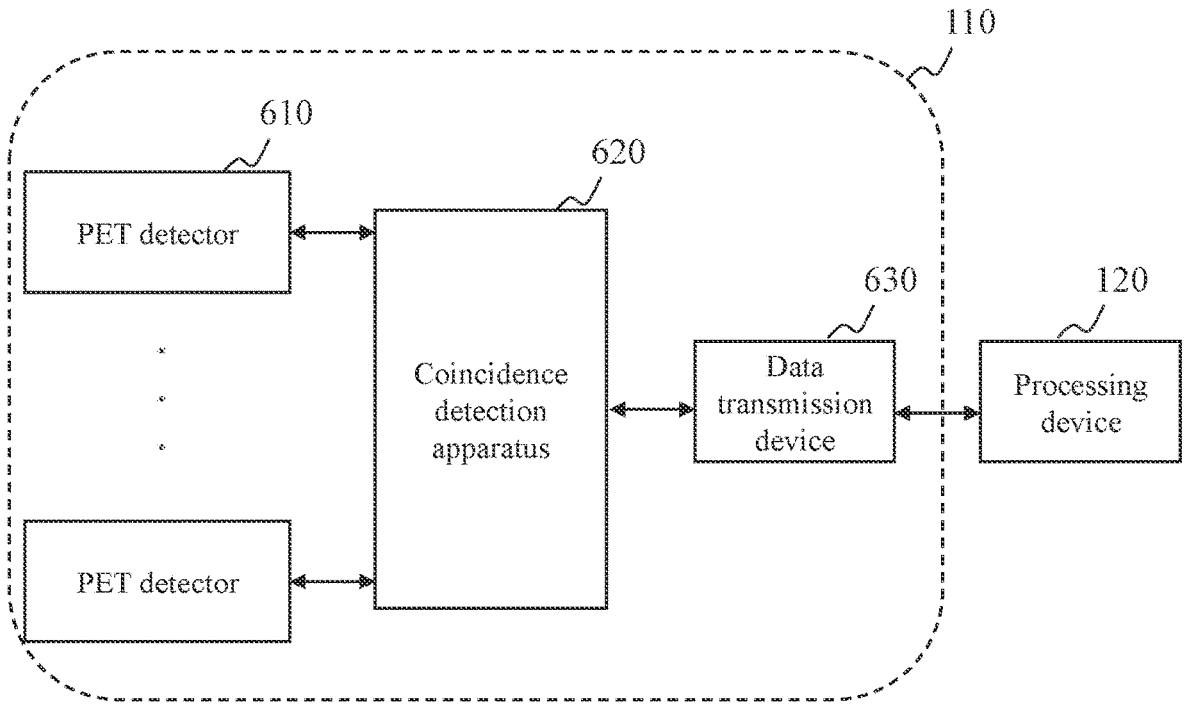
FIG. 6 is a schematic diagram illustrating a transmission path of the first coincidence data according to some embodiments of the present disclosure.

For example, the buffering and transmission process of the first coincidence data may be described in combination with FIG. 6. FIG. 6 is a schematic diagram illustrating a transmission path of the first coincidence data according to some embodiments of the present disclosure. The scanner 110 may include a plurality of detectors 610, a coincidence detection apparatus 620, and a data transmission device 630 (also referred to as a data transmission link). The plurality of detectors 610 may detect multiple pair of photons from the subject injected with a radionuclide at a preset injected dose (e.g., 0.1 millicurie per kilogram (mCi/kg) and generate detected signals. Exemplary radionuclides may include F18-Fluorodeoxyglucose (FDG), F18-fluorodopa (FDOPA), C11-methionine (MET), etc. The detected signals may be used to generate the first coincidence data. The coincidence detection apparatus 620 may be communicatively connected with the plurality of detectors 610. The coincidence detection apparatus 620 may detect, buffer, read, and/or write the first coincidence data or a portion thereof. For example, the coincidence detection apparatus 620 may include a coincidence detection module configured to detect the first coincidence data and one or more buffer memories. The one or more buffer memories may implement the buffering of the first coincidence data or a portion thereof. The data transmission device 630 may be communicatively connected with the coincidence detection apparatus 620. The data transmission device 620 may receive coincidence data (i.e., the third coincidence data) outputted by the coincidence detection apparatus 620, and transmit the received coincidence data or a portion thereof to the processing device 120 via the network 150.

As shown in FIG. 6, the first coincidence data may be transmitted by the coincidence detection apparatus 620 to the processing device 120 through the data transmission device 630 in the transmission path of the first coincidence data. When a high-activity radionuclide is used (e.g., injected into the subject), gamma photons detected by the plurality of detectors 610 of the scanner 110 may increase. The gamma photons detected by the PET detectors may be used to determine the first coincidence data by the coincidence detection module of the coincidence detection apparatus 620. Accordingly, a data volume of the first coincidence data may also increase. In some cases, a bandwidth of each of at least a part of one or more buffer memories of the coincidence detection apparatus 620 may be below a volume of coincidence data to be stored in the buffer memory. For example, a writing bandwidth of a buffer memory may be greater than a reading bandwidth of the buffer memory. The reading bandwidth refers to a volume of data (e.g., coincidence data) readable from the buffer memory per unit time such that at least a portion of the first coincidence data may be not written into the buffer memory and data loss may occur in the buffering of the first coincidence data. The writing bandwidth refers to a volume of data (e.g., coincidence data) to be written into the buffer memory per unit time. In some other cases, the transmission path may be unstable under poor network quality. In such cases, data loss may occur on the transmission path of the at least a portion of the first coincidence data outputted by the coincidence detection apparatus 620. Data lost in the coincidence detection apparatus 620 and the data transmission device 630 may be referred to as the missing data of the first coincidence data. Due to the presence of the missing data, a processing result (e.g., a preliminary SUV determined based on the second coincidence data) of the processing device 120 may be inaccurate.

In some embodiments, the data loss of the first coincidence data occurred in the coincidence detection apparatus 620 may be resulted from the buffering of the first coincidence data. The data loss occurred in the data transmission device 630 may be resulted form the transmission of the first coincidence data. The missing data may include a first portion resulted from the buffering of the first coincidence data (e.g., in the coincidence detection apparatus 620) and/or a second portion resulted from the transmission of the first coincidence data (e.g., in the data transmission device 630). Thus, the count of the missing data includes a first missing count of the first portion of the missing data (also referred to as first missing count for brevity) resulted from the buffering of the first coincidence data and/or a second missing count of the second portion of the missing data (also referred to as second missing count for brevity) resulted from the transmission of the first coincidence data.

In some embodiments, the processing device 120 may obtain the count of the missing data from at least one counting device (e.g., the first counting device 710, the first counting device 710, the second counting device 910, and/or the third counting device 1010). The at least one counting device may be configured to monitor at least a portion of the missing data, and record a count of the portion of the missing data. Details regarding the obtaining of the count of the missing data may be found elsewhere in the present disclosure. See, for example, FIGS. 7-10 and the descriptions thereof.

In 520, the processing device 120 (e.g., the obtaining module 410 or the processor 210) may obtain second coincidence data and a second count of the second coincidence data.

The second coincidence data may be coincidence data received by the processing device (e..g, the processing device 120). Since data loss occurs in the buffering and transmission process of the first coincidence data, the second coincidence data may be a portion of the first coincidence data (e.g., the remainder of the first coincidence data after the data loss, or a portion of the third coincidence data). The second coincidence data and the missing data may constitute the first coincidence data.

In some embodiments, the processing device 120 may obtain the second coincidence data by receiving the second coincidence data transmitted by the scanner 110 (e.g., the data transmission device 630 of the scanner 110) actively. Alternatively, the processing device 120 may obtain the second coincidence data by transmitting a data acquisition request to the scanner 110 (e.g., the data transmission device of the scanner 110) at a preset interval (e.g., 1 second, 5 seconds, 10 seconds, 20 seconds, 1 minute, 2 minutes, etc.). In response to the data acquisition request, the scanner 110 (e.g., the data transmission device 630 of the scanner 110) may transmit the second coincidence data to the processing device 120. After the processing device 120 receives the second coincidence data, a count of the second coincidence data (also referred to as second count of the second coincidence data or second count) may be obtained.

In 530, the processing device 120 (e.g., the compensation module 420 or the processor 210) may perform a compensation relating to the second coincidence data based on at least two of the count of the missing data, a first count of the first coincidence data, or the second count of the second coincidence data.

In some embodiments, the compensation relating to the second coincidence data may be performed on one or more parameters associated with the subject, the second count of the second coincidence data, a PET image of the subject, etc. The one or more parameters may relate to the second coincidence data and/or the second count of the second coincidence data. For example, the one or more parameters may include a Standard Uptake Value (SUV), a radioactivity concentration, etc.

Merely by way of example, a compensation relating to the second coincidence data performed on the SUV may be described for illustration purposes, which is not intended to be limiting. The processing device 120 may determine a parameter value (e.g., a preliminary SUV) of the SUV of the subject based on the second count of the second coincidence data. The preliminary SUV refers to a preliminary value of a SUV of a target tissue of the subject. The SUV may relate to a radioactivity concentration in the target tissue of the subject, a dose injected to the subject (also referred to as injected dose), and a body weight of the subject. The radioactive concentration of the target tissue may be determined based on the second count of the second coincidence data. For example, a PET image may be generated by reconstructing the second coincidence data. Each of pixel values of pixels in the PET image may represent the radioactive concentration at a portion of the subject corresponding to the pixel value. The PET image may be determined based on a distribution of a PET tracer in the subject. A difference between different distributions of the PET tracer may be reflected by different radioactive concentrations represented by different grey levels or pseudo colors. Grey levels of the PET image may indicate radioactive concentrations of the PET tracer, which may be observed visually or analized quantitatively, such as using the SUV.

In some embodiments, the preliminary SUV may be determined according to Equation (1):

$$SUV_{pre} = \frac{Ac}{D \cdot 2^{\left(\frac{-\Delta t}{T_{1/2}}\right)}} \cdot W, \tag{1}$$

where $SUV_{pre}$ denotes the preliminary SUV, Ac denotes the radioactivity concentration in the target tissue, D denotes the injected dose, W denotes the body weight of the subject, $\Delta t$ denotes a delay between a start time point of the injection and a start time point of the scan, and $T_{1/2}$ denotes a half-life of the radionuclide injected into the subject. A unit of the radioactivity concentration may be kilo-Becquerel per milliliter (Kbq/ml). A unit of the injected dose may be mega-Becquerel (Mbp). A unit of the body weight may be kilogram (Kg). According to Equation (1), for each pixel in a target region of the PET image, the preliminary SUV may positively correlate to the radioactive concentration, and the radioactive concentration may positively correlate to a count of a portion of the second coincidence data corresponding to the pixel. In this way, an accuracy of image analysis regarding the PET image may be improved after the preliminary SUV is compensated.

The processing device 120 may determine a compensation coefficient for compensating the preliminary SUV. Due to the presence of the missing data, the second count of the second coincidence data may be below a count of the first coincidence data (also referred to as first count of the first coincidence data or first count), the preliminary SUV may be inaccurate. The compensation coefficient may be a coefficient for compensating the effect of the missing data on the SUV. The processing device 120 may determine the compensation coefficient based on at least two of the count of the missing data, the first count of the first coincidence data, or the second count of the second coincidence data.

In some embodiments, a compensation coefficient determination model may be obtained. The compensation coefficient may be determined based on the compensation coefficient determination model, and at least two of the count of the missing data, the first count of the first coincidence data, or the second count of the second coincidence data. In some embodiments, the compensation coefficient determination model may be a trained machine learning model. The trained machine learning model may be obtained by training a machine learning model based on training input data and training target data. Exemplary machine learning models may include a neural network model (e.g., a deep learning model), a deep belief network (DBN), a stacked auto-encoders (SAE), a logistic regression (LR) model, a support vector machine (SVM) model, a decision tree model, a naive Bayesian model, a random forest model, or a restricted Boltzmann machine (RBM), a gradient boosting decision tree (GBDT) model, a LambdaMART model, an adaptive boosting model, a hidden Markov model, a perceptron neural network model, a Hopfield network model, or the like, or any combination thereof. Exemplary neural network models may include a deep neural network (DNN) model, a convolutional neural network (CNN) model, a recurrent neural network (RNN) model, a feature pyramid network (FPN) model, etc. Exemplary CNN models may include a V-Net model, a U-Net model, a FB-Net model, a Link-Net model, or the like, or any combination thereof. The compensation coefficient may be determined based on the trained machine learning model based on the count of the missing data and the second coincidence data.

In some embodiments, the training input data (e.g., at least two of a sample count of sample missing data, a first sample count of sample first coincidence data, or a second sample count of sample second coincidence data) and corresponding training target data (e.g., target compensation coefficient(s)) may be input into the machine learning model. The machine learning may be trained based on the training input data and the corresponding training target data to obtain the compensation coefficient determination model.

The training process of the compensation coefficient determination model may include one or more iterations for iteratively updating value(s) of one or more model parameters of the machine learning model based on the training data until a termination condition is satisfied in a certain iteration. Exemplary termination conditions may include that a value of a loss function obtained in the certain iteration is less than a threshold value, that a preset count of iterations have been performed, that the loss function converges such that the difference of the values of the loss function obtained in a previous iteration and the current iteration is within a threshold value, etc. The loss function may be used to measure a discrepancy between an output of the (partially) machine learning model in an iteration and the corresponding training target data. Exemplary loss functions may include a focal loss function, a log loss function, a cross-entropy loss, a Dice ratio, or the like. After the training process is terminated, the compensation coefficient determination model may be determined. The compensation coefficient may be determined based on the compensation coefficient determination model, the count of the missing data, and the second coincidence data.

Alternatively, the processing device 120 may determine a ratio relating to at least two of the count of the missing data, the first count of the first coincidence data, or the second count of the second coincidence data. The first count of the first coincidence data may be equal to a sum of the count of the missing data and the second count of the second coincidence data. The ratio may be determined as the compensation coefficient. In some embodiments, the processing device 120 may determine a first ratio of the first count of the first coincidence data to the count of the missing data. The first ratio may be determined as the compensation coefficient. For example, the count of the missing data may be a, the second count of the second coincidence data may be b, and the first ratio may be (a+b)/a, which may be determined as the compensation coefficient. In some embodiments, the processing device 120 may determine a second ratio of the first count of the first coincidence data to the second count of the second coincidence data. The second ratio may be determined as the compensation coefficient. For example, the second ratio may be (a+b)/b. In some embodiments, the processing device 120 may determine a third ratio according to experiments or empirical judgements. The third ratio may be determined as the compensation coefficient.

The processing device 120 may generate a compensated SUV by compensating the preliminary SUV using the compensation coefficient. Since the second coincidence data is merely a portion of the first coincidence data, the preliminary SUV calculated based on the second coincidence data may be smaller than an actual SUV calculated based on the first coincidence data. In such a case, the preliminary SUV may be compensated, and a compensated preliminary SUV (also referred to as compensated SUV for brevity) may be generated, which may have a higher accuracy than the preliminary SUV.

In some embodiments, the compensated SUV may be generated by multiplying the preliminary SUV by the compensation coefficient. The compensation coefficient, which may be the ratio of the first coincidence data to the missing data or the second coincidence data, may reflect the effect of the missing data on the first coincidence data. The compensated SUV determined by multiplying the preliminary SUV by the compensation coefficient may be much closer to the actual SUV calculated based on the first coincidence data, thus improving the accuracy of subsequent diagnoses and/or treatments. It should be note that the compensated SUV may also be generated based on a compensation model, the preliminary SUV, the second coincidence data, and the count of the missing data. The compensation model may be a trained machine learning model.

As another example, the processing device 120 may perform a compensation on the second count of the second coincidence data, which may be described for illustration purposes. In some embodiments, the processing device 120 may determine a compensation coefficient. For instance, the processing device 120 may determine the compensation coefficient according to the embodiments set forth above, which is not repeated here. The processing device 120 may compensate the second count of the second coincidence data using the compensation coefficient. For example, the compensated second count be determined by multiplying the second count by the compensation coefficient.

In some embodiments, the compensated SUV may be determined based on the compensated second count. Merely by way of example, the compensated SUV may be determined based on the compensated second count according to Equation (2):

$$SUV_{comp} = \frac{Ac'}{D \cdot 2^{\left(\frac{-\Delta t}{T_{1/2}}\right)}} \cdot W, \tag{2}$$

where $SUV_{comp}$ denotes the compensated SUV, Ac' denotes the compensated radioactivity concentration in the target tissue. As stated above, the preliminary SUV may positively correlate to the radioactive concentration, and the radioactive concentration may positively correlate to second count of the second coincidence data. The compensated SUV may positively correlate to compensated radioactive concentration, and the compensated radioactive concentration may positively correlate to compensated second count.

As another example, the processing device 120 may perform a compensation on the second coincidence data, which may be described for illustration purposes. In some embodiments, the processing device 120 may determine a compensation coefficient. For instance, the processing device 120 may determine the compensation coefficient according to the embodiments set forth above, which is not repeated here. The processing device 120 may generate compensated second coincidence data (also referred to as compensated coincidence data) by compensating the second coincidence data using the compensation coefficient. In some embodiments, the processing device 120 may duplicate a portion of the second coincidence data according to the compensation coefficient. For example, if the compensation coefficient is 1.5, the processing device 120 may duplicate a half of the second coincidence data randomly. The compensated coincidence data may be generated by combining the duplicated portion of the second coincidence data and the second coincidence data.

As still a further example, the processing device 120 may generate a compensated PET image of the subject may be described below for illustration purposes. The processing device 120 may reconstruct a PET image (i.e., the compensated PET image) of the subject based on the compensated coincidence data described above.

Figure 7:
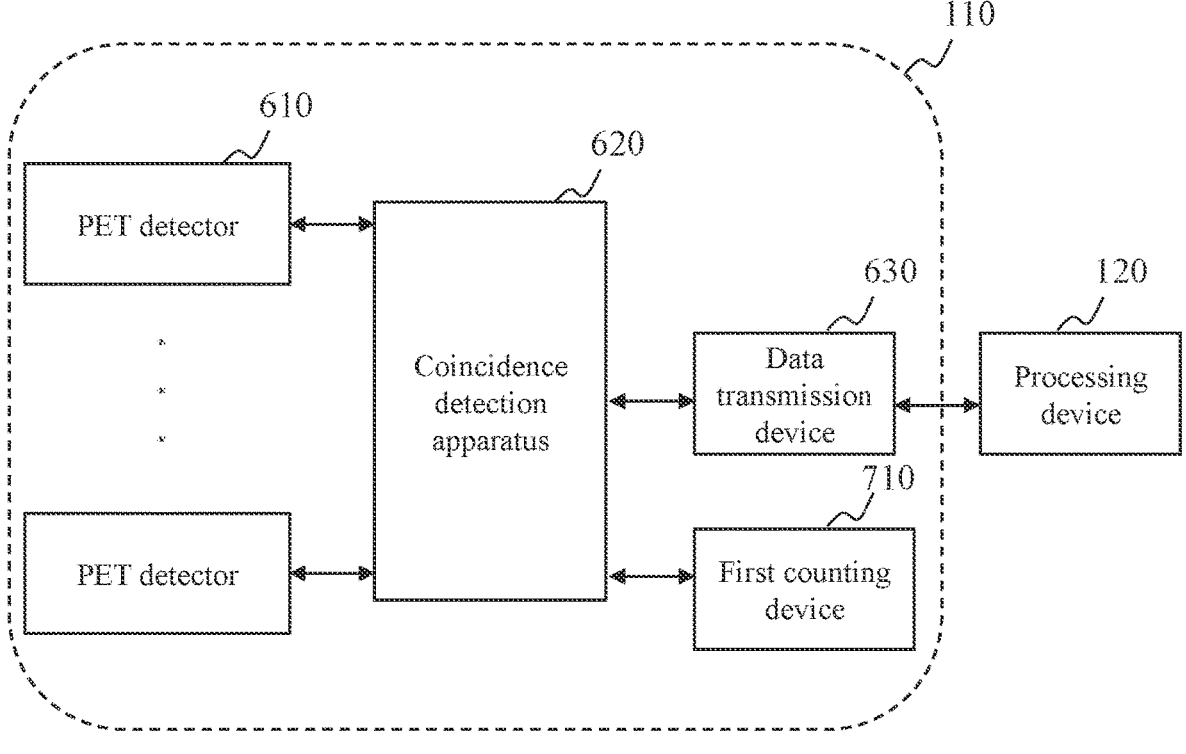
FIG. 7 is a schematic diagram illustrating the obtaining of the first missing count of the first portion of the missing data resulted from the buffering of the first coincidence data according to some embodiments of the present disclosure.

FIG. 7 is a schematic diagram illustrating the obtaining of the first missing count of the first portion of the missing data resulting from the buffering of the first coincidence data according to some embodiments of the present disclosure.

As shown in FIG. 7, the scanner 110 may include a first counting device 710. The first counting device 710 may be connected with the coincidence detection apparatus 620. The first counting device 710 may monitor the buffering of the first coincidence data to monitor the first portion of the missing data, and record the first missing count of the first portion of the missing data. In some embodiments, the first counting device 710 may monitor the buffering of the first coincidence data and record the first missing count at a unit time. The unit time may be a specific time period set as a cycle for monitoring the buffering of the first coincidence data and recording the first missing count. The unit time may be 1 second, 10 seconds, 1 minute, 5 minutes, etc.

The data cache module of the coincidence detection apparatus 620 may include one or more buffer memories configured for the buffering of the first coincidence data or a portion thereof. In some embodiments, the first counting device 710 may obtain signals (e.g., a writing signal, a full signal, etc.) relating to statuses of the one or more buffer memories. The first counting device 710 may determine the first missing count of the first portion of the missing data based on the obtained signals. Details regarding the obtaining of the first missing count of the first portion of the missing data resulted from the buffering of the first coincidence data may be found elsewhere in the present disclosure. See, for example, FIG. 8 and the descriptions thereof.

In some embodiments, the first counting device 710 may record the first missing count and combine the first missing count with the third coincidence data output from the coincidence detection apparatus 620 to be transmitted to the data transmission device 630. In this way, the first missing count may be transmitted to the processing device 120 together with the second coincidence data. The processing device 120 may obtain the second coincidence data and the first missing count simultaneously.

Figure 8:
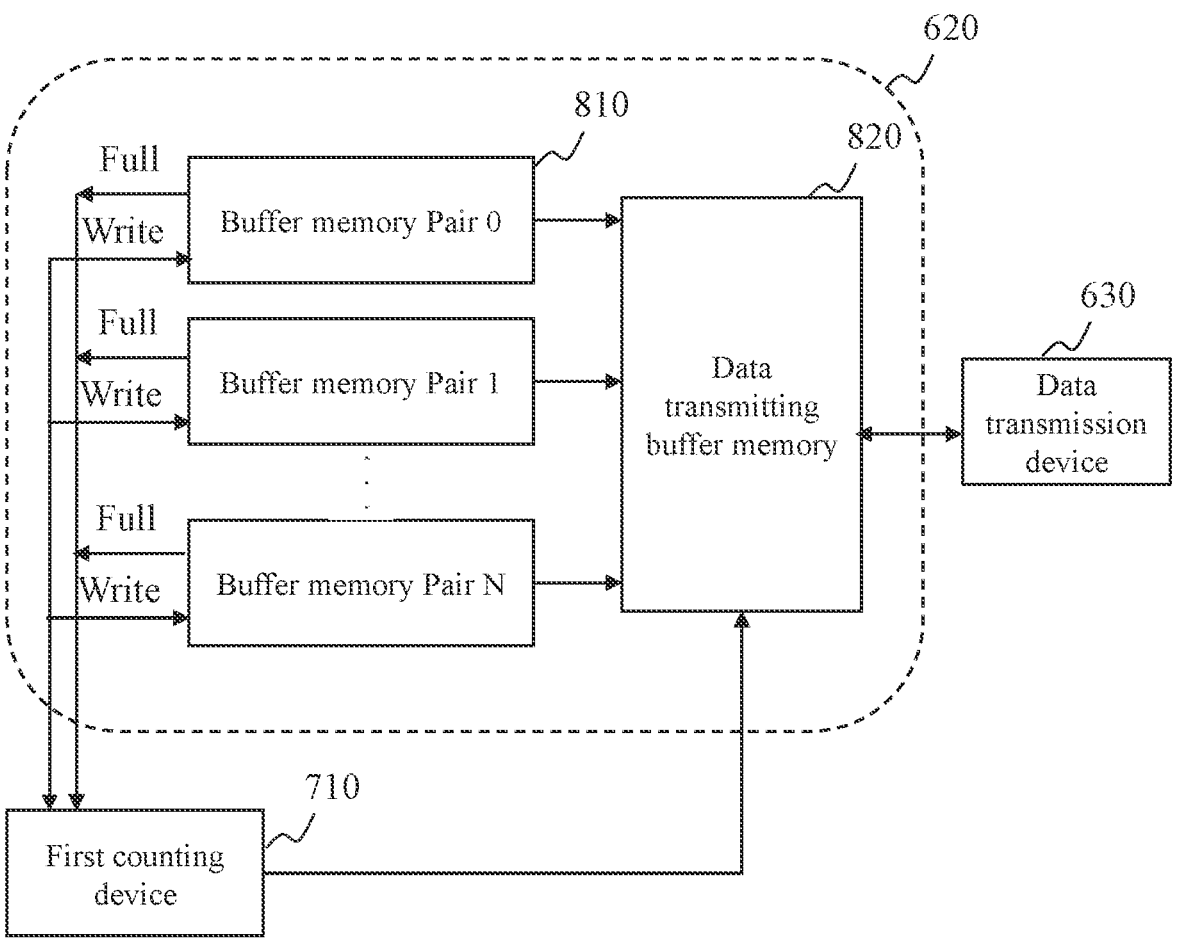
FIG. 8 is a schematic diagram illustrating the obtaining of the first missing count of the first portion of the missing data resulted from the buffering of the first coincidence data according to some embodiments of the present disclosure.

FIG. 8 is a schematic diagram illustrating the obtaining of the first missing count of the first portion of the missing data resulted from the buffering of the first coincidence data according to some embodiments of the present disclosure.

As shown in FIG. 8, the coincidence detection apparatus 620 may (at least) include one or more of buffer memories 810, a data transmitting buffer memory 820, and the first counting device 710. Each of the one or more buffer memories 810 may correspond to a pair of PET detectors on a same LOR, and configured to store at least a portion of corresponding coincidence data determined based on detected signals acquired by the pair of PET detectors. Coincidence data (i.e., a portion of the first coincidence data) corresponding to different pairs of PET detectors may be stored in different buffer memories. In some embodiments, a correspondence relationship between the one or more buffer memories 810 and one or more pairs of PET detectors may be established. At least a portion of coincidence data determined by the coincidence detection module based on detected signals acquired by a pair of PET detectors at different time points (that the coincidence data is generated) may be stored in sequence according to a chronological order, in a corresponding buffer memory determined based on the correspondence relationship. For example, at least a portion of the coincidence data corresponding to different time points may be arranged in a queue according to the chronological order. Coincidence data at a headmost position of the queue may be stored in a corresponding buffer memory at the earliest; coincidence data at a backmost position of the queue may be stored in a corresponding buffer memory at the latest.

The data transmitting buffer memory 820 may receive coincidence data stored in the one or more buffer memories 810 and transmit at least a portion of the coincidence data to the data transmission device 630. In some embodiments, the data transmitting buffer memory 820 may receive coincidence data from each of the one or more buffer memories in turn. For instance, in a cycle, the data transmitting buffer memory 820 may receive coincidence data at a headmost position of a first buffer memory Pair 0, the data transmitting buffer memory 820 may receive coincidence data at a headmost position of a second buffer Pair 1, . . . , and the data transmitting buffer memory 820 may receive coincidence data at a headmost position of a (N+1)-th buffer memory Pair N. N may be an integer larger than 0. The (N+1)-th buffer memory Pair N may correspond to a pair of PET detectors marked with Pair N. Then the data transmitting buffer memory 820 may receive coincidence events from the N+1 buffer memories similarly in a next cycle. The data transmitting buffer memory 820 may transmit the received coincidence data to the data transmission device 630 in sequence according to an order in which the coincidence data is received by the data transmitting buffer memory 820.

The first counting device 710 may be connected with the one or more buffer memories 810 and the data transmitting buffer memory 820. The first counting device 710 may monitor the buffering of the first coincidence data and record the first missing count at a unit time. In some embodiments, the first counting device 710 may obtain signals (e.g., a writing signal, a full signal, etc.) relating to statuses of the one or more buffer memories 810. The writing signal relating to a buffer memory refers to a signal indicating that the system (e.g., the coincidence detection module of the coincidence detection apparatus 620) is writing coincidence data into the buffer memory. If the system is writing coincidence data into the buffer memory, the first counting device 710 may receive a writing signal relating to the buffer memory. The full signal relating to a buffer memory refers to a signal indicating that the buffer memory is fully stored, and subsequent coincidence data may not able to be written into the buffer memory and may be lost. If the buffer memory is fully stored, the first counting device 710 may receive a full signal relating to the buffer memory.

When a high-activity radionuclide is used (e.g., injected into the subject), gamma photons detected by the PET detectors of the scanner 110 may increase. The gamma photons detected by the PET detectors may be processed by the coincidence detector apparatus (e.g., the coincidence detection module of the coincidence detection apparatus 620) for determining the first coincidence data. The first coincidence data may be transmitted to the one or more buffer memories 810. In some cases, a bandwidth of each of at least a part of the one or more buffer memories may be below a volume of the first coincidence data to be stored in the buffer memory. If a writing bandwidth of a buffer memory is greater than a reading bandwidth of the buffer memory, the buffer memory may be fully stored.

In some embodiments, the first counting device 710 may detect a full signal of at least a part of the one or more buffer memories 810. The detected full signal(s) may indicate that the at least a part of the one or more buffer memories 810 is fully stored. After detecting the full signal, each time one of the at least a part of one or more buffer memories 810 receives a first writing signal, the first missing count may be increased by one. The first missing count may equal a total count of first writing signals received by the at least a part of one or more buffer memories 810 when one or more full signals are received from the at least a part of one or more buffer memories 810 within the unit time.

In some embodiments, the first counting device 710 may be configured to monitor the first writing signals. The first counting device 710 may record the first missing count and write the first missing count into the data transmitting buffer memory 820. The first missing count may be combined with the third coincidence data to be transmitted to the data transmission device 620. In this way, the first missing count may be transmitted to the processing device 120 together with the second coincidence data. The processing device 120 may obtain the second coincidence data and the first missing count simultaneously.

Figure 9:
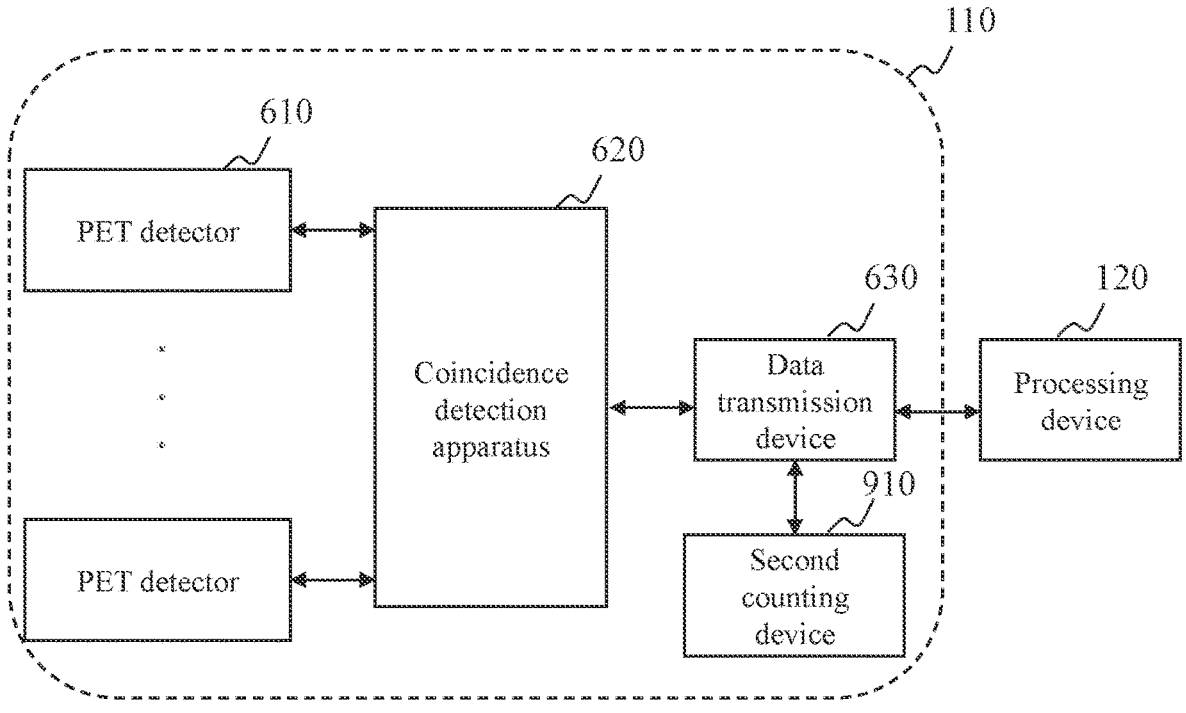
FIG. 9 is a schematic diagram illustrating the obtaining of a second missing count of the second portion of the missing data resulted from the transmission of the first coincidence data according to some embodiments of the present disclosure.

FIG. 9 is a schematic diagram illustrating the obtaining of a second missing count of the second portion of the missing data resulted from the transmission of the first coincidence data according to some embodiments of the present disclosure.

As shown in FIG. 9, the scanner 110 may include a second counting device 910. The second counting device 910 may be connected with a transmission device of the first coincidence data. The transmission device may be connected between the coincidence detection apparatus 620 and processing device 120. In some embodiments, the second counting device 910 may be connected to the data transmission device 630. In some embodiments, the second counting device 910 may be configured to monitor an output of the coincidence detection apparatus 620. In this way, the second counting device 910 may monitor the transmission of at least a portion of the first coincidence data outputted by the coincidence detection apparatus 620 (i.e., the third coincidence data) for monitoring the second portion of the missing data, and record the second missing count of the second portion of the missing data. In some embodiments, the second counting device 910 may monitor the transmission of the third coincidence data and record the second missing count at a unit time. The unit time may be a specific time period set as a cycle for monitoring the second portion of the missing data and recording the second missing count. The unit time may be 1 second, 10 seconds, 1 minute, 5 minutes, etc.

Factors such as a poor network, an unstable transmission chain (when a high activity radionuclide is used), etc., may cause a random data loss of the third coincidence data occurred in the data transmission device 630. The second portion of the missing data in the random data loss may not have a tendency or follow a law. The second counting device 910 may record a total count of coincidence data input into the data transmission device 630 (i.e., the third count of the third coincidence data output by the coincidence detection apparatus 620) and a total count of coincidence data output from the data transmission device 630 (i.e., the second count of the second coincidence data received by the processing device 120). The second missing count may be determined based on the third count of the third coincidence data output by the coincidence detection apparatus 620 and the total count of coincidence data output from the data transmission device 630 (i.e., the second count of the second coincidence data received by the processing device 120). For instance, the second missing count may equal a difference between the third count of the third coincidence data output by the coincidence detection apparatus 620 and the second count of the second coincidence data received by the processing device 120 within the unit time.

In some embodiments, the second counting device 910 may record the second missing count and combine the second missing count with the coincidence data (e.g., the second coincidence data) to be transmitted to the processing device 120. In this way, the second missing count may be transmitted to the processing device 120 together with the second coincidence data. The processing device 120 may obtain the second coincidence data and the second missing count simultaneously.

According to the embodiments set forth above, the second counting device 910 may monitor the total counts of coincidence data input into and output from the data transmission device 630 so as to determine the second missing count, thus rendering the determination of the second missing count to be convenient and easy to implement. In addition, the accuracy of the second missing count may be improved by monitoring an input port and an output port of the data transmission device 630.

Figure 10:
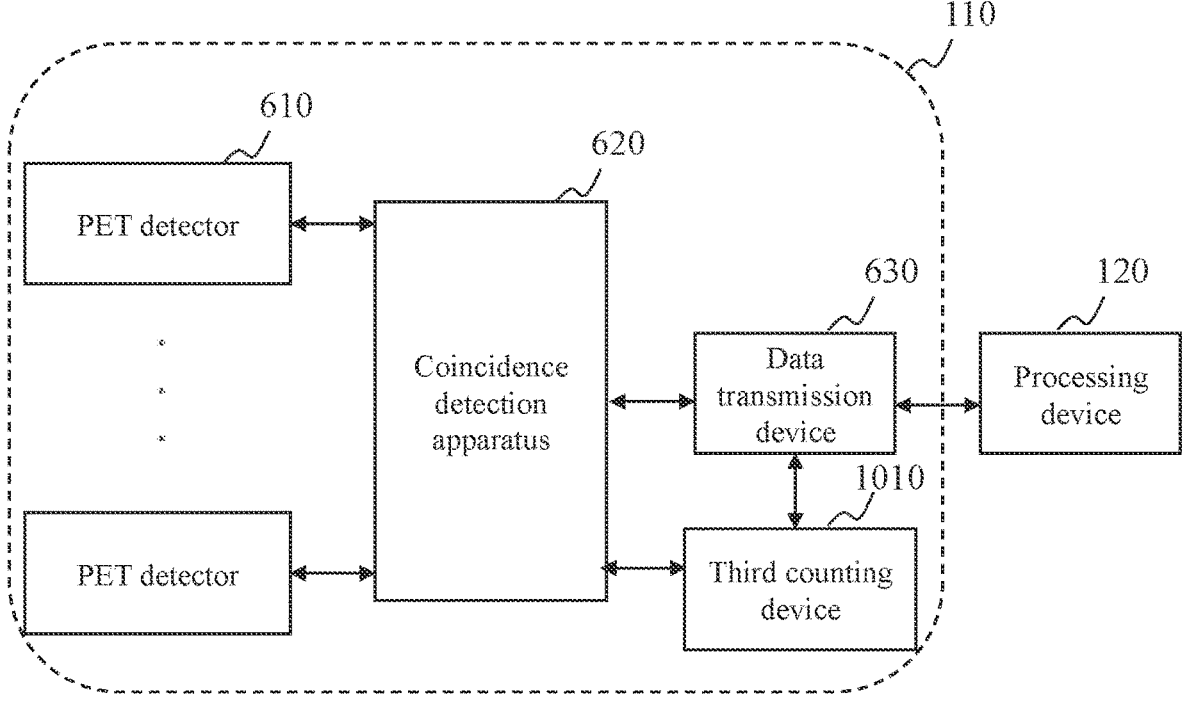
FIG. 10 is a schematic diagram illustrating the obtaining of the count of the missing data according to some embodiments of the present disclosure.

FIG. 10 is a schematic diagram illustrating the obtaining of the count of the missing data according to some embodiments of the present disclosure.

As shown in FIG. 10, the scanner 110 may include a third counting device 1010. Since data loss occurs in both the coincidence detection apparatus 620 and the data transmission device 630. The coincidence detection apparatus 620 and the data transmission device 630 may be regarded as a whole so as to determine the count of the missing data. In some embodiments, the third counting device 1010 may be connected with both the coincidence detection apparatus 620 and the data transmission device 630. In some embodiments, the third counting device 1010 may monitor coincidence data generated by the coincidence detection module of the coincidence detection apparatus 620 and coincidence data output from the data transmission device 630. A difference between the count of the coincidence data generated by the coincidence detection module of the coincidence detection apparatus 620 and the count of the coincidence data output from the data transmission device 630 may be determined as the count of the missing data. The coincidence data generated by the coincidence detection module of the coincidence detection apparatus 620 may be the first coincidence data, and the count of the coincidence data generated by the coincidence detection module of the coincidence detection apparatus 620 may be the first count of the first coincidence data. The coincidence data output from the data transmission device 630 may be the second coincidence data, and the count of the coincidence data output from the data transmission device 630 may be the second count of the second coincidence data. The count of the missing data may equal a difference between the first count of the first coincidence data and the second count of the second coincidence data within the unit time.

In some embodiments, the third counting device 1010 may obtain the first missing count X1 according to the embodiments as described in FIGS. 7 and 8. The third counting device 1010 may obtain the second missing count X2 according to the embodiments as described in FIG. 9. The count of the missing data may equal a sum of the first missing count X1 and the second missing count X2. The first missing count X1 may be a sum of a count of data loss of coincidence data in each of the one or more buffer memories 810. The second missing count X2 may be a difference between a total count A of coincidence data input into the data transmission device 630 and a total count B of coincidence data input into the processing device 120 (i.e., the second count of the second coincidence data).

FIG. 11 includes a flowchart illustrating an exemplary process for obtaining a count of missing data in a transmission path of the first coincidence data according to some embodiments of the present disclosure. In some embodiments, the process 1100 may be performed by the second missing data counting device and the third missing data counting device. In some embodiments, the process 1100 may be performed by the fourth missing data counting device.

In 1110, the third counting device 1010 may detect one or more full signals of at least a part of the one or more buffer memories in the coincidence detection apparatus.

In 1120, the third counting device 1010 may monitor writing signals received by the at least a part of the one or more buffer memories.

In 1130, the third counting device 1010 may determine a first missing count of a first portion of the missing data according to a count of the writing signals.

In 1140, the third counting device 1010 may obtain a third count of third coincidence data outputted by the coincidence detection apparatus and a second count of second coincidence data input into the processing device.

In 1150, the third counting device 1010 may determine a difference between the third count of third coincidence data output by the the coincidence detection apparatus and the second count of second coincidence data input into the processing device as a second missing count of a second portion of the missing data.

In 1160, the third counting device 1010 may determine the count of the missing data by summing up the first missing count and the second missing count.

In some embodiments, the operations 1110 through 1160 of the process 1100 may be performed in a way the same as or similar to the approaches provided with reference to FIGS. 7-10, which are not repeated here.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

What is claimed is:

1. A system, comprising:
at least one storage medium including a set of instructions; and
at least one processor configured to communicate with the at least one storage medium, wherein when executing the set of instructions, the at least one processor is configured to direct the system to perform operations including:
obtaining a count of missing data of first coincidence data;
obtaining second coincidence data and a second count of the second coincidence data, the second coincidence data and the missing data constituting the first coincidence data;
performing a compensation relating to the second coincidence data based on at least two of the count of the missing data, a first count of the first coincidence data, or the second count of the second coincidence data, wherein the performing a compensation relating to the second coincidence data based on at least two of the count of the missing data, a first count of the first coincidence data, or the second count of the second coincidence data includes:
determining a preliminary Standard Uptake Value (SUV) based on the second coincidence data;
determining a compensation coefficient based on the at least two of the count of the missing data, the first count of the first coincidence data, or the second count of the second coincidence data;
generating a compensated SUV by compensating the preliminary SUV using the compensation coefficient; and
compensating the second count of the second coincidence data using the compensation coefficient.

2. The system of claim 1, wherein the count of the missing data includes at least one of a first missing count and a second missing count, the first missing count being resulted from buffering of the first coincidence data, and the second missing count being resulted from transmission of a portion of the first coincidence data.

3. The system of claim 2, wherein the first missing count equals a total count of first writing signals being received by at least a part of one or more buffer memories, each of the first writing signals being received when a full signal is received from one of the at least a part of one or more buffer memories, the one or more buffer memories being configured for the buffering of the first coincidence data.

4. The system of claim 3, wherein the first missing count is detected by a first counting device, the first counting device being configured to monitor the first writing signals.

5. The system of claim 2, wherein the second missing count equals a difference between a third count of third coincidence data outputted by a coincidence detection apparatus and the second count of the second coincidence data, a data transmission device being configured for the transmission of the first coincidence data.

6. The system of claim 5, wherein the second missing count is detected by a second counting device, the second counting device being configured to monitor an output of the coincidence detection apparatus.

7. The system of claim 1, wherein the determining a compensation coefficient based on the at least two of the count of the missing data, the first count of the first coincidence data, or the second count of the second coincidence data includes:
obtaining a compensation coefficient determination model; and
determining the compensation coefficient based on the compensation coefficient determination model and the at least two of the count of the missing data, the first count of the first coincidence data, or the second count of the second coincidence data.

8. The system of claim 1, wherein the generating a compensated SUV by compensating the preliminary SUV using the compensation coefficient includes:
generating the compensated SUV by multiplying the preliminary SUV by the compensation coefficient.

9. The system of claim 1, wherein the determining a compensation coefficient based on the at least two of the count of the missing data, the first count of the first coincidence data, or the second count of the second coincidence data includes:
determining a ratio relating to the at least two of the count of the missing data, the first count of the first coincidence data, or the second count of the second coincidence data; and
designating the ratio as the compensation coefficient.

10. The system of any one of claims claim 1, wherein the performing a compensation relating to the second coincidence data based on at least two of the count of the missing data, a first count of the first coincidence data, or the second count of the second coincidence data includes:
compensating the second count of the second coincidence data using the compensation coefficient.

11. The system of claim 1, wherein the count of the missing data includes a second missing count, the second missing count being resulted from transmission of a portion of the first coincidence data.

12. A method implemented on a computing device having a processor and a computer-readable storage device, the method comprising:
obtaining a count of missing data of first coincidence data;
obtaining second coincidence data and a second count of the second coincidence data, the second coincidence data and the missing data constituting the first coincidence data;
performing a compensation relating to the second coincidence data based on at least two of the count of the missing data, a first count of the first coincidence data, or the second count of the second coincidence data, wherein the performing a compensation relating to the second coincidence data based on at least two of the count of the missing data, a first count of the first coincidence data, or the second count of the second coincidence data includes:

determining a preliminary Standard Uptake Value (SUV) based on the second coincidence data;

determining a compensation coefficient based on the at least two of the count of the missing data, the first count of the first coincidence data, or the second count of the second coincidence data;

generating a compensated SUV by compensating the preliminary SUV using the compensation coefficient; and compensating the second count of the second coincidence data using the compensation coefficient.

13. The method of claim 12, wherein the count of the missing data includes at least one of a first missing count or a second missing count, the first missing count being resulted from buffering of the first coincidence data, and the second missing count being resulted from transmission of a portion of the first coincidence data.

14. The method of claim 13, wherein the first missing count equals a total count of first writing signals being received by at least a part of one or more buffer memories, each of the first writing signals being received when a full signal is received from one of the at least a part of one or more buffer memories, the one or more buffer memories being configured for the buffering of the first coincidence data.

15. The method of claim 14, wherein the first missing count is detected by a first counting device, the first counting device being configured to monitor the first writing signals.

16. The method of claim 13, wherein the second missing count equals a difference between a third count of third coincidence data outputted by a coincidence detection apparatus and the second count of the second coincidence data, a data transmission device being configured for the transmission of the first coincidence data.

17. The method of claim 16, wherein the second missing count is detected by a second counting device, the second counting device being configured to monitor an output of the coincidence detection apparatus.

18. The method of claim 12, wherein the determining a compensation coefficient based on the at least two of the count of the missing data, the first count of the first coincidence data, or the second count of the second coincidence data includes:

determining a ratio relating to the at least two of the count of the missing data, the first count of the first coincidence data, or the second count of the second coincidence data; and designating the ratio as the compensation coefficient.

19. A non-transitory readable medium, comprising at least one set of instructions, wherein when executed by at least one processor of a computing device, the at least one set of instructions directs the at least one processor to perform a method, the method comprising:

obtaining a count of missing data of first coincidence data;

obtaining second coincidence data and a second count of the second coincidence data, the second coincidence data and the missing data constituting the first coincidence data;

performing a compensation relating to the second coincidence data based on at least two of the count of the missing data, a first count of the first coincidence data, or the second count of the second coincidence data, wherein the performing a compensation relating to the second coincidence data based on at least two of the count of the missing data, a first count of the first coincidence data, or the second count of the second coincidence data includes:

determining a preliminary Standard Uptake Value (SUV) based on the second coincidence data;

determining a compensation coefficient based on the at least two of the count of the missing data, the first count of the first coincidence data, or the second count of the second coincidence data;

generating a compensated SUV by compensating the preliminary SUV using the compensation coefficient; and compensating the second count of the second coincidence data using the compensation coefficient.

* * * * *